United States Patent
Ege et al.

(10) Patent No.: US 8,789,422 B2
(45) Date of Patent: Jul. 29, 2014

(54) ELECTROMAGNETIC-ACOUSTIC TRANSDUCER AND ULTRASONIC TEST SYSTEM HAVING THE SAME

(75) Inventors: Michael Ege, Schlaitdorf (DE); Jürgen Wanner, Pfullingen (DE)

(73) Assignee: Institut Dr. Foerster GmbH & Co. KG (DE)

( * ) Notice: Subject to any disclaimer, the term of this patent is extended or adjusted under 35 U.S.C. 154(b) by 564 days.

(21) Appl. No.: 13/125,499

(22) PCT Filed: Oct. 9, 2009

(86) PCT No.: PCT/EP2009/007251
§ 371 (c)(1),
(2), (4) Date: Jun. 23, 2011

(87) PCT Pub. No.: WO2010/046036
PCT Pub. Date: Apr. 29, 2010

(65) Prior Publication Data
US 2011/0259108 A1    Oct. 27, 2011

(30) Foreign Application Priority Data
Oct. 24, 2008   (DE) .......................... 10 2008 054 250

(51) Int. Cl.
*G01N 29/22* (2006.01)

(52) U.S. Cl.
USPC .............................. 73/643; 324/262; 310/336

(58) Field of Classification Search
CPC ..... G01N 29/225; G01N 29/2412; B06B 1/04
USPC ................... 73/643, 632, 635, 644; 324/262; 310/322, 323.21, 336
See application file for complete search history.

(56) References Cited

U.S. PATENT DOCUMENTS

| 4,258,319 A | * | 3/1981 | Shimada et al. | ............. 324/226 |
| 4,259,637 A | * | 3/1981 | Bloomfield et al. | .......... 324/166 |
| 4,314,203 A | * | 2/1982 | Haberlein | ..................... 324/262 |

(Continued)

FOREIGN PATENT DOCUMENTS

| DE | 36 14 069 A1 | 11/1987 |
| DE | 42 28 426 C1 | 3/1994 |

(Continued)

OTHER PUBLICATIONS

Alers, G.A., "Electromagnetic Introduction of Ultrasonic Waves: EMAT, EMUS, EMAR," *EMAT Consulting*, 2004, 1 sheet Abstract and 8 pages of article.

*Primary Examiner* — Peter Macchiarolo
*Assistant Examiner* — Samir M Shah
(74) *Attorney, Agent, or Firm* — DLA Piper LLP (US)

(57) ABSTRACT

An electromagnetic-acoustic transducer for ultrasonic testing of test objects which are composed substantially of an electrically conductive material includes a magnet system that produces a magnetic field intended to penetrate into the test object, and an inductive coil arrangement that produces an electromagnetic alternating field superimposed on this magnetic field in the test object, and that detects electromagnetic alternating fields emitted from the test object, wherein magnet system is arranged in a magnetization unit, the coil arrangement is arranged in a probe unit separate from the magnetization unit, the probe unit is mounted such that it can move relative to the magnetization unit in the area of the magnetic field.

15 Claims, 4 Drawing Sheets

(56) References Cited

U.S. PATENT DOCUMENTS

| | | | | |
|---|---|---|---|---|
| 4,337,662 A | * | 7/1982 | Kopineck et al. | 73/632 |
| 4,495,953 A | * | 1/1985 | Bennewitz | 607/136 |
| 4,793,185 A | | 12/1988 | Boettger et al. | |
| 5,140,860 A | * | 8/1992 | Huschelrath et al. | 73/643 |
| 5,164,921 A | * | 11/1992 | Graff et al. | 367/140 |
| 5,233,972 A | * | 8/1993 | Rattner | 601/4 |
| 5,619,423 A | | 4/1997 | Scrantz | |
| 6,109,108 A | * | 8/2000 | Ohtani et al. | 73/599 |
| 6,717,397 B2 | * | 4/2004 | Sorenson, Jr. | 324/126 |
| 7,395,715 B2 | * | 7/2008 | Salzburger et al. | 73/643 |
| 8,079,266 B2 | * | 12/2011 | Nichiforenco et al. | 73/643 |
| 2003/0112000 A1 | * | 6/2003 | Sorenson, Jr. | 324/126 |
| 2006/0236764 A1 | * | 10/2006 | Salzburger et al. | 73/577 |
| 2008/0276711 A1 | * | 11/2008 | Nichiforenco et al. | 73/643 |

FOREIGN PATENT DOCUMENTS

| | | | | |
|---|---|---|---|---|
| DE | 4228426 C1 | * | 3/1994 | G01N 29/04 |
| DE | 199 15 099 A1 | | 10/2000 | |
| DE | 19915099 A1 | * | 10/2000 | G01N 29/22 |
| DE | 11 2005 000 106 T5 | | 1/2007 | |
| DE | 11 2006 001 894 T5 | | 6/2008 | |
| JP | 60-108749 | | 6/1985 | |
| RU | 2 246 106 C2 | | 9/2004 | |
| RU | 58714 U1 | | 11/2006 | |
| RU | 2 325 638 C1 | | 5/2008 | |
| WO | 2005/083419 A1 | | 9/2005 | |
| WO | 2007/013836 A1 | | 2/2007 | |
| WO | WO 2007013836 A1 | * | 2/2007 | G01N 29/04 |

* cited by examiner

ELECTROMAGNETIC-ACOUSTIC TRANSDUCER AND ULTRASONIC TEST SYSTEM HAVING THE SAME

RELATED APPLICATIONS

This is a §371 of International Application No. PCT/EP2009/007251, with an international filing date of Oct. 9, 2009 (WO 2010/046036 A1, published Apr. 29, 2010), which is based on German Patent Application No. 10 2008 054 250.4, filed Oct. 24, 2008, the subject matter of which is incorporated by reference.

TECHNICAL FIELD

This disclosure relates to an electromagnetic acoustic transducer for ultrasound testing of test objects composed substantially of electrically conductive material, and to an ultrasound test system which has at least one such electromagnetic acoustic transducer.

BACKGROUND

Ultrasound testing is a non-destructive, acoustic test method for testing test objects composed of materials which conduct sound, such as metals. Ultrasound testing is attractive for many applications, particularly because of the capability to also detect internal defects which are located under the surface of the test object. In conventional ultrasound-based test systems, the ultrasound waves which are used for testing are produced by a piezoelectric transducer, and are introduced into the test object via a coupling medium, for example, water.

Electromagnetic acoustic transducers (EMATs) are an alternative to this conventional ultrasound technology, and can be used for testing all sufficiently electrically conductive materials. An electromagnetic acoustic transducer, which is also referred to for short in the following text as an EMAT, is used to produce ultrasound waves directly in the material of the test object, based on the electromagnetic principle. For this purpose, an EMAT has a magnet system for production of a magnetic field, which is intended to penetrate into the test object, and an inductive coil arrangement for production of an electromagnetic alternating field, which is superimposed on this magnetic field in the test object, and for detection of electromagnetic alternating fields emitted from the test object. The coil arrangement which has been excited by high-frequency AC voltage induces eddy currents in the area close to the surface of the test object. The charge carriers which are moved in this case are in this case moved in the magnetic field which is produced in the test object by the magnet system. The Lorentz force which is produced acts as a periodic force on the solid body structure of the material of the test object and in this way produces ultrasound waves directly within the test object, which ultrasound waves propagate in the material of the test object and can be used for testing. Therefore, in principle, ultrasound testing by an EMAT does not require any coupling medium, for example, water, thus allowing EMAT technology to also be used, for example, for testing metals in the hot state. Ultrasound testing by EMAT can be used both for fault testing in metals and metal alloys and for determination of geometric parameters, such as wall thickness, diameter and the like, of test objects composed of electrically conductive material.

DE 11 2005 000 106 T5 (which corresponds to WO 2005/083419) describes a conventional electromagnetic acoustic transducer which has a housing with a working surface facing the test object. A magnet system having permanent magnets for production of a continuous magnetic field, as well as an inductive coil arrangement, in the vicinity of the working surface, for electromagnetic production of scanning pulses and for reception of pulses emitted from the test object are arranged in the housing. The magnet system has at least three permanent magnets, which have a rectangular cross section and are arranged immediately adjacent to, and parallel to, the working surface of the EMAT in the housing. In this case, the central magnet has vertical polarization with respect to the working surface, while each of the adjacent magnets at the side have horizontal polarization. Magnetic flux concentrators are fitted between the permanent magnets of the magnet system and the coil arrangement such that the magnetic flux originating from the central magnet is in each case concentrated onto an induction coil which is fitted under a concentrator. The EMAT formed in this way is intended to have high sensitivity and a fairly broad working range, and to be physically compact at the same time.

WO 2007/013836 A1 discloses an electromagnetic acoustic transducer having an outer housing and an inner housing, which is fitted within the outer housing. The magnet system, with a plurality of permanent magnets, is accommodated in the inner housing. The inductive coil arrangement and the associated magnetic field concentrators are fitted to a mounting plate in the outer housing such that, when the inner housing is in a working position, the permanent magnetic field produced by the magnet system is concentrated on the coil arrangement. The inner housing is fitted such that it can move within the outer housing such that it can be moved away from the working position (magnetic flux contact with the coil arrangement) by linear movement or rotation with the aid of a drive which is fitted to the outer housing, this allowing the EMAT to be taken out of use. The aim of this is to make it possible to quickly lift the transducer off a test object without this being impeded by the magnetic field produced by the magnet system.

While testing, the inductive coil arrangement should be located as close as possible to the surface of the test object to achieve a high test sensitivity. To protect the coil arrangement in the case of known electromagnetic acoustic transducers, a protection device composed of wear-resistant material, for example, in the form of a ceramic protection plate, is located in front of the coil arrangement, that is to say between the coil arrangement and the surface of the test object. To avoid increasing the distance between the coils of the coil arrangement and the test object any more than necessary, the material of the protection layer should have only a small thickness. As a further constraint, the material should not, be significantly electrically conductive, because of the principle of the method for production of the ultrasound.

In general, electromagnetic acoustic transducers are used within a test apparatus to carry out the test process in an automated manner. In this case, an EMAT is passed over the surface of a test object to be examined such that the entire area of the test object to be examined can be covered. In industrial use, it is desirable for the test time to be as short as possible in this case to maximize the throughput of tested material. Relatively high relative speeds between the EMAT and the material of the test object are therefore desirable.

When testing ferromagnetic materials, relatively strong magnetic attraction forces can occur between the test objects and an EMAT that is being passed along the surface of the test object, and this can lead to considerable wear to the protection elements when there is a sliding contact between the EMAT and the surface of the test object, particularly when the relative speeds are relatively high.

As an alternative, the surface of the test object can be scanned without any touching contact by having a small air gap between the surface of the test object and the EMAT, which air gap should be at least sufficiently large that collisions do not occur, or occur only rarely, between the EMAT and the material of the test object, for example, because of irregularities on the surface of the test object. However, any increase in the distance between the surface of the test object and the coil arrangement results in a drastic decrease in the test sensitivity.

It could therefore be helpful to provide an electromagnetic acoustic transducer for ultrasound testing which allows test objects to be scanned at a high relative speed, but without significant restrictions in terms of the life of the EMAT or the test sensitivity.

SUMMARY

We provide an electromagnetic acoustic transducer for ultrasound testing of test objects which are composed substantially of an electrically conductive material including a magnet system that produces a magnetic field intended to penetrate into the test object, and an inductive coil arrangement that produces an electromagnetic alternating field superimposed on this magnetic field in the test object, and that detects electromagnetic alternating fields emitted from the test object, wherein the magnet system is arranged in a magnetization unit, the coil arrangement is arranged in a probe unit separate from the magnetization unit, and the probe unit is mounted such that it can move relative to the magnetization unit in the area of the magnetic field.

We also provide a test apparatus for ultrasound testing of test objects composed substantially of electrically conductive material including at least one electromagnetic acoustic transducer.

DETAILED DESCRIPTION

An electromagnetic acoustic transducer has a magnet system for production of a magnetic field, which is intended to penetrate into the test object, and an inductive coil arrangement for production of an electromagnetic alternating field, which is superimposed on the magnetic field in the test object, and for detection of electromagnetic alternating fields emitted from the test object. In this case, the magnet system is arranged in a magnetization unit, and the coil arrangement is arranged in a probe unit which is separate from the magnetization unit, and the probe unit is mounted such that it can move relative to the magnetization unit in the area of the magnetic field.

The probe unit is not rigidly connected to the magnetization unit but is held such that it can move with respect to the latter, thus allowing the probe unit to be moved toward or away from the magnetization unit when the transducer is operated relative to the magnetization unit. In particular, an intermediate space without any material and of variable size may be located between the magnetization unit and the probe unit, the size and/or thickness of which intermediate space changes when the two units are moved relative to one another. This allows ferromagnetic test material to be tested while maintaining a sliding contact between the probe unit and the surface of the test object, with high test sensitivity and with little wear occurring, since the strong magnetic attraction force between the magnetization unit and the ferromagnetic test material has no influence, or only a very minor influence, on the force with which the probe unit rests on the surface of the test object.

Because of the relative movement of the probe unit with respect to the magnetization unit and because of the lack of rigid coupling between the magnetization unit and the probe unit, the mass to be moved while moving over surface irregularities can be relatively small, thus allowing the probe unit to follow the surface of the test object without any problems, and without any excessive inertial forces occurring, which could result in wear to the transducer, or could even lead to destruction.

Particularly in an industrial environment, testing frequently has to be carried out in severe environmental conditions, for example, on test objects which are still hot and have scaly surfaces. For applications such as these, examples are advantageous in which an intermediate space of variable size is located between the magnetization unit and the probe unit, and in which the intermediate space is encapsulated in a contamination-proof manner with the aid of a flexible casing. This makes it possible to ensure that no dirt can enter the intermediate space between the magnetization unit and the probe unit while nevertheless at the same time ensuring that the two units can move relative to one another. By way of example, the flexible casing may be formed by a bellows composed of suitable flexible material, wherein the bellows may be, in particular, in the form of a plastic bellows or a leather bellows.

There are various possible ways to hold the probe unit in the correct relative position with respect to the magnetization unit and at the same time to ensure the desired limited capability for the probe unit to move relative to the magnetization unit. One possibility is for the probe unit to be attached to the magnetization unit with the aid of an elastically flexible holder. The holder can be designed such that, when no force is present, the probe unit assumes its nominal position at the nominal distance from the magnetization unit, and can leave this nominal position under the influence of external forces. The elastically flexible holder may be the only holder for the probe unit. It is particularly advantageously possible for the elastically flexible holder to be formed by a bellows which can at the same time also seal the intermediate space between the magnetization unit and the probe unit in a contamination-proof manner, thus carrying out a dual function. Otherwise, it is also possible for the magnetization unit to be attached to a first holding device and for the probe unit to be attached to a second holding device which is separate from the first holding device. The holding devices can be fitted independently of one another to a mount for the transducer, in an articulated manner, or in some other manner such that they can move. In one refinement, the second holding device, which holds the probe unit, is connected in an articulated manner to the first holding device. This makes it possible to move the combination of the magnetization unit and the probe unit, that is to say the entire EMAT, by movement of the first holding device, while the probe unit is moved with respect to the magnetization unit by relative movement of the first holder with respect to the second holder.

If required, one or more magnetic field concentrators may be provided between the magnetization unit and the probe unit. However, in some electromagnetic acoustic transducers, the intermediate space between the magnet system and the coil arrangement is free of magnetic field concentrators. This makes it possible to considerably reduce the distance between the magnet system and the coil arrangement in comparison to conventional EMATs. The increase in the test sensitivity which can be achieved by reducing the separation makes it possible to partially or entirely compensate for the effect of the lack of magnetic field concentration.

The arrangement in which the intermediate space between the magnet system and the coil arrangement is free of magnetic field concentrators can also be provided for electromagnetic acoustic transducers with a fixed predetermined distance and/or rigid coupling between the magnet system and the coil arrangement.

In some instances, a nominal distance between the magnet system and the coil arrangement is less than 8 mm, in which case the distance may also be less than 7 mm, less than 6 mm, or less than 5 mm. If the distance between the coil arrangement and the magnetization unit is variable in a limited form, the distance may, for example, vary by ±2 mm, or by ±3 mm about a nominal distance of 3 mm, 4 mm or 5 mm. The distance between the magnet system and the coil arrangement may also be greater.

To prevent the possibility of a critical touching contact between the probe unit and the magnetization unit in extraordinary operating conditions, according to one example, a spacer device is provided to limit the mutual deflection between the magnetization unit and the probe unit to a finite minimum separation, thus precluding a touching contact between these assemblies which move relative to one another. A layer composed of elastically flexible material or some other impact-damping device can be located between the probe unit and the magnetization unit. The impact-damping layer may be formed by a section of the bellows material.

In one example, spacers with supporting sections for directly supporting the spacers on the surface of the test object are fitted to a housing of the magnetization unit, wherein the spacers are of such a size that, when the spacers strike the surface of the test object, a small separation still remains between the magnetization unit and the probe unit which has been pressed to the maximum extent in the direction of the magnetization unit.

The coil arrangement may be designed in a conventional manner. However, novel coil arrangements have been developed which allow the best test results in particular even in the absence of magnetic field concentrators. One example of a coil arrangement has a plurality of individual coils which are arranged alongside one another, wherein line sections of immediately adjacent individual coils overlap one another into an overlap area. The individual coils are normally coils without cores and with one or more windings, the windings defining a coil axis. The overlap area may in each case be located centrally between adjacent coil axes. If immediately adjacent individual coils are switched in antiphase in a coil arrangement such as this, such that they can be operated, during operation of the apparatus, with the opposite phase or with a 180° phase offset from one individual coil to the next, then this results in undesirable contributions of those line sections of the individual coils which overlap in the overlap area cancelling one another out. Particularly in these situations, it is then possible to completely dispense with the use of magnetic field concentrators, in favor of a shorter distance between the magnetization unit and the probe unit. This is very good for the sensitivity of the EMAT.

The coil arrangement may be formed with wound individual coils. If the coil arrangement is in the form of conductor tracks which are fitted to a possibly flexible mounting plate composed of electrically insulating material, the joint installation and removal during initial assembly and during maintenance or repair are particularly simple. The conductor tracks can be fitted to the mounting plate by printing or by some other coating method.

While test material is being tested or measured, the EMAT can scan the material surface without touching it in such a way that there is a small air gap between the probe unit and the material surface, for example, with a thickness of up to about 5 mm. It is also possible for the probe unit to make touching contact with the material surface, and to slide on it during relative movement. If a material surface is not flat, because of the flexibility and capability to move with respect to the magnetization unit, the probe unit can follow this surface even if the magnetization unit does not change its position.

Various measurement tasks can be carried out using an electromagnetic acoustic transducer designed. These include fault detection of (one-dimensional) point defects, (two-dimensional) area defects or beads, as well as three-dimensional volume defects on the surface or in the interior of a test object. Furthermore, a number of geometric parameters, such as the material thickness, the wall thickness of a tube and/or distances can be determined in the test material. Finally, it is also possible to determine certain material characteristics, such as the hardness or elastic constants. All sufficiently electrically conductive materials may be considered as a material for the test object, for example, various steels or materials containing nickel or cobalt, or else non-ferrous metals such as aluminum, copper and many other metals. The transducer can be used on various test geometries, for example, for continuous measurement of elongated objects such as rods or tubes with a rolled or bare surface, plates or other semi-finished products, or else for measurement of finished components with various geometries.

The disclosure also relates to a test apparatus for ultrasound testing of test objects composed substantially of an electrically conductive material. This is characterized by the fact that it has at least one electromagnetic acoustic transducer.

These and further features will become evident not only from the claims but also from the description and the drawings, in which case the individual features may each be implemented in their own right or in groups in the form of sub-combinations of an example, or in other fields, and may represent advantageous examples.

Figure 1:
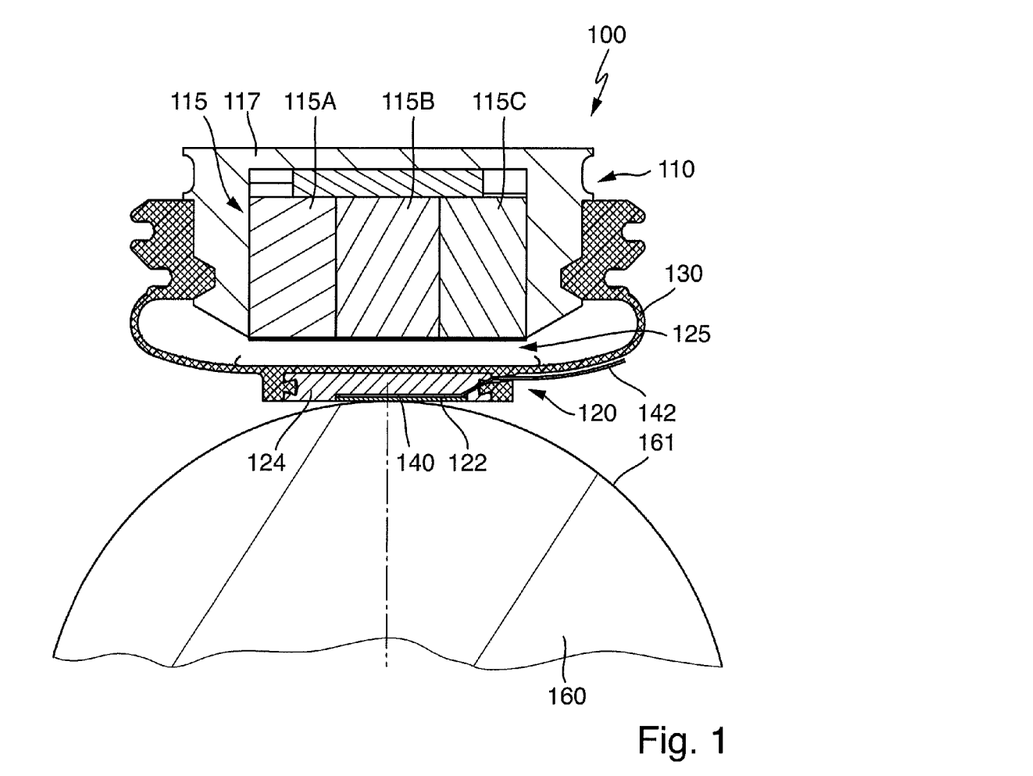
FIG. 1 shows a cross section through one example of an electromagnetic acoustic transducer, which is in sliding contact with a cylindrical surface of a round rod as a test object.

FIG. 1 shows a cross section through one example of an electromagnetic acoustic transducer (EMAT) 100, which is in sliding contact with a cylindrical surface 161 of a test object 160 in the form of a cylindrical rod composed of a ferromagnetic steel. The EMAT has a magnetization unit 110 and a probe unit 120, which is separate from it and is connected such that it can move to the magnetization unit via a bellows 130, which is closed at both ends and composed of elastic plastic material such that the position of the probe unit relative to the magnetization unit is continuously variable with deformation of the bellows and an increase or decrease, associated with this, in the distance between them. In this case, the probe unit is always located in the area of the magnetic field which is produced from the magnet system. An intermediate space 125 is located between the magnetization unit and the probe unit 120, which is arranged at a distance therefrom, which intermediate space 125 is free of material, has a variable volume, is surrounded all the way round at the sides by the bellows 130, and is therefore protected against the ingress of dust or other contamination from the outside.

The magnetization unit 110 comprises a magnet system 115 for production of a constant magnetic field, which penetrates into areas of the test object 160 close to the surface during operation of the EMAT. In the example, the magnet system 115 consists of cuboid permanent magnets 115A, 115B, 115C of different polarity, wherein the central permanent magnet 115B is polarized substantially radially or at right angles to the surface of the test object, while the outer magnets 115A, 115C, which are immediately adjacent on the outside, are polarized at right angles thereto, and substantially parallel to the surface of the test object. A ferromagnetic plate 116 is fitted on the side of the permanent magnets facing away from the probe unit, for magnetic shielding of the magnetic field. The permanent magnets and the shielding plate are permanently installed in a housing 117, which closes the magnetization unit on the side facing away from the test object.

The number and shape of the magnets of the magnet system may also differ from those illustrated. In particular, the magnetic field can also be produced using electromagnets. In general, the magnetic field produced by the magnet system is a constant field, although it is also possible to use electromagnets to produce a lower-frequency or higher-frequency alternating field. The flux density concentration on the surface of the test object can be set and varied by controlling the frequency of the alternating field.

The probe unit 120 contains an inductive coil arrangement 140, one example of which will be explained in more detail later with reference to FIGS. 3 and 4. This arrangement 140 may comprise coils of various designs, which can be arranged in various ways. To protect the coils, a thin protection plate 122 is located in front of the coil arrangement on the side facing the test object, which protection plate 122 is composed of an electrically non-conductive or poorly conductive material with high mechanical wear resistance. In the example, the protection plate is composed of a composite ceramic, in which ceramic, fibers are bonded in a ceramic matrix. The coil arrangement and the protection plate are jointly mounted in a flat recess in a mounting frame 124 which is resistant to twisting, is composed of an electrically non-conductive material, and has dovetail grooves on the narrow side surfaces that are illustrated to mount the mounting frame in a flexible receptacle in the bellows 130. Since the probe unit 120 is fitted to the outside of the bellows, a section of the bellows material is located between the probe unit and the magnetization unit and forms an elastically flexible intermediate layer which, as a spacer, prevents direct touching contact between the mounting frame of the probe unit 120 and the magnetization unit 110, and can damp any impacts. The coil arrangement 140 is connected by electrical connecting lines 142, to control electronics, which are not illustrated, for the test apparatus.

During use of the EMAT, the magnetization unit 110 produces a strong magnetic field in the area of the probe unit 120 and in areas of the test object 160 close to the surface. The coil arrangement contains excitation coils which produce a high-frequency electromagnetic excitation alternating field when appropriately operated with high-frequency AC voltage, which field is superimposed on the magnetic field of the magnet system 115 and likewise penetrates into areas of the test object close to the surface. The excitation coils are connected to suitable electronics and therefore able to produce short ultrasound pulses in the material of the test object, whose frequency may, for example, be in the MHz range. To allow ultrasound pulses to be produced in this case, the material of the test object (test material) must at least have an electrical conductivity such that moving charge carriers are produced in the test material, which move in the magnetic field of the magnetization unit, act on the lattice structure of the material of the test object under the influence of the Lorentz force, and therefore produce ultrasound waves directly in the material of the test object. The material of the test object is preferably ferromagnetic. The type of ultrasound (frequency, alignment) which is produced in the material of the test object depends on the direction of the magnetic field produced by the magnet system as well as on the configuration of the excitation coils in the inductive coil arrangement, and the electronics.

Coils for detection of signal alternating fields emitted from the material of the test object are also located in the coil arrangement. These are coils likewise connected to suitable electronics and suitable for receiving reflected ultrasound signals from the material of the test object. These receiving coils may be identical to the transmitting coils (excitation coils), although coils which are separate therefrom may also be provided. Statements relating to flaws in the material of the test object, possibly as well as statements relating to geometric parameters of the test material (for example, the diameter, thickness or wall thickness) can be made by evaluation of the received signals. It is also possible to determine various elastic parameters of the test material from the emitted signals.

The process of excitation and reception of ultrasound signals is also referred to in this application as testing. During testing, a relative movement generally takes place between the EMAT and the test object. It is also possible to dispense with a relative movement between the EMAT and the test object, for example, for wall thickness measurements on tubes. To produce a desired relative movement, it is possible, for example, to move only the EMAT relative to the (stationary) test object. It is also possible for the EMAT to be stationary and for only the test object to be moved, for example, rotationally and/or translationally. It is also possible to move both components. During relative movement, the probe unit 120 of the EMAT is moved relative to the surface 161 of the test object 160. The extent to which the tested surface is covered (completely or with gaps) in this case depends on the requirements of the test task.

During this movement, the probe unit 120, which is mounted by the bellows 130 such that it is elastically flexible, can follow the surface of the test material. In this case, the probe unit is in general pressed by elastic forces by the bellows, and possibly by centrifugal forces, slightly against the surface of the test object, in which case, however, the pressure force is sufficiently low that only a small amount of wear takes place when there is a sliding contact between the surface 161 of the test object and the protection plate 122. The work can also be carried out contactlessly, phase-by-phase. For example, if there is a surface projection in the test path that is being covered, then the relatively low-mass probe unit can follow the projection by moving away in the direction of the magnetization unit, in which case the air gap 125 is then briefly reduced. Depending on the condition of the surface, the size of the air gap between the magnetization unit and the probe unit of the EMAT may therefore vary to a greater or lesser extent. Ventilation channels, which are not shown, in this case ensure that the entire arrangement can "breathe" as the volume within the bellows varies without dirt particles being able to enter the internal area of the bellows.

The capability of the probe unit to move in an advantageous manner relative to the magnetization unit is assisted if the magnetization unit on the one hand and the probe unit on the other hand are attached to different holders, that is to say to holders which can move independently of one another. One example will also be explained in conjunction with FIG. 5. In the example shown in FIG. 1, the magnetization unit 110 is attached to a holder which is not shown, while the probe unit 120 is held directly on the magnetization unit via the bellows 130, which act as a holder. It is therefore possible for one of the two holders (in this case the holder for the probe unit) to be attached to the other holder (the holder for the magnetization unit). It is also possible to use only one holder. In any case, the holding devices for the probe unit and for the magnetization unit can be designed in a suitable manner to ensure that the strong magnetic attraction force between the magnetization unit 110 and the ferromagnetic test material has no influence on the force between the probe unit 120 and the material surface. Therefore, only small contact-pressure forces occur between the probe unit and the surface of the test object even when testing ferromagnetic material in the strong magnetic field of the magnet system, thus making it possible to considerably lengthen the life of the probe unit, in comparison to conventional systems.

If magnetic scaling or other impurities occur while the test is being carried out, this has no negative effects on the operation of the transducer in the illustrated example, because the intermediate space 125 between the magnetization unit 110 and the probe unit 120 is sealed in a dust-tight manner by the bellows 130.

By way of example, electromagnetic acoustic transducers may be subject to considerable mechanical, thermal and other loads when used in an industrial environment associated with manufacture, which loads have a disadvantageous effect on the life of the transducer, and could lead to production delays in the event of premature wear or failure resulting from damage. A number of protection mechanisms will now be explained with reference to FIG. 2, which can be provided individually or in combination on a transducer to ensure that it can operate reliably even in severe measurement environments. Functional elements and functional groups which have already been explained with reference to FIG. 1 are identified by the same reference symbols in the longitudinal section illustration in FIG. 2 as those in FIG. 1.

Figure 2:
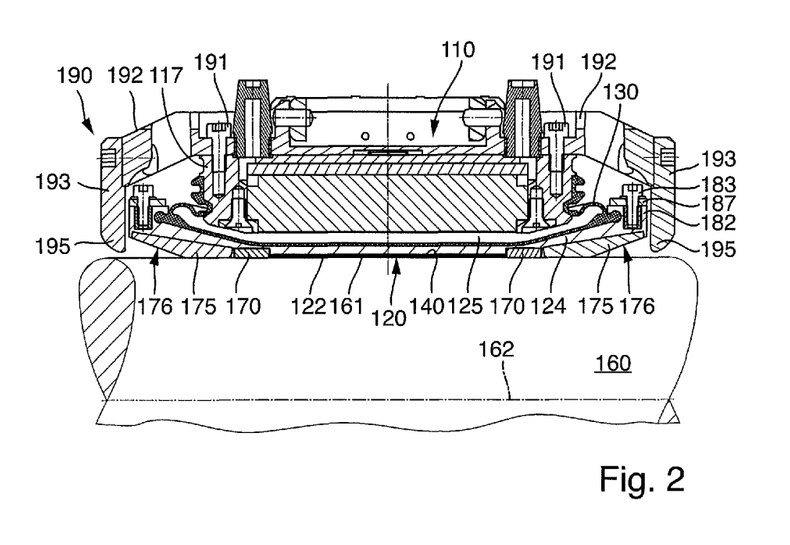
FIG. 2 shows a longitudinal section through the arrangement shown in FIG. 1, with protection apparatuses for protection of the measurement arrangement against mechanical damage.

The coil arrangement 140 and the protection plate 122 which is provided for its protection are arranged in a flat recess in a mounting frame 124 which is composed of electrically insulating or poorly conductive material and extends in the illustrated longitudinal direction both forward and to the rear, beyond the area of the coil arrangement, obliquely in the direction of the magnetization unit, that is to say away from the test object. Relatively flat, first protection elements 170 composed of wear-resistant material, for example, a metal or a ceramic, are arranged immediately adjacent to the recess for the probe arrangement and the protection plate, and their flat outer surfaces, which face the test object, are located virtually flush with the outside of the protection plate 122, but projecting somewhat toward the test object. Since these elements project minimally above the protection plate, a sliding contact generally takes place only via these elements, and only via the protection plate as well if the surface of the test object has relatively sharp curvature. Skids 175 are connected to each of the protection elements on the outside, which skids 175 are composed of wear-resistant material, for example, a ceramic, which are mounted in an appropriate recess on the front face of the frame 124, facing the test object, and have the inclined surfaces 176, which run at an acute angle, in each case rising outward, to the working surface of the transducer, which is defined by the outer face of the protection plate. If the EMAT is now moved relative to the surface 161 of the test object with a movement component parallel to the longitudinal axis 162 of the test object, and if this surface of the test object has local uneven areas in the form of projections, then these could damage the protection plate, and possibly the coil arrangement, when passing over them. This is prevented with the aid of the skids 175 and the protection elements 170 since, when a projection occurs on the surface of the test object, these first of all strike the inclined surface of a skid and, as the movement progresses, the entire probe unit 120 would be raised in the direction of the magnetization unit, reducing the thickness of the intermediate space 125, before the uneven area runs into the area of the probe arrangement. This therefore reliably prevents an impact-like load on the sensitive protection plate as can occur, for example, when a test object runs into or out of a rotating head.

Furthermore, the example in FIG. 2 shows that it is possible not only to attach the probe unit 120 to the magnetization unit via the bellows 130 but that (alternatively or additionally), a separate holding device can also be provided for the probe unit. For this purpose; threaded holes 182 which are directed upward, that is to say away from the test object, are provided in the frame, on the end areas of the frame 124 which are located in the longitudinal direction, and allow a holding device 187, which will be explained in more detail in conjunction with FIG. 5, for the probe unit to be attached with the aid of attachment screws 183.

In addition to the components already described, FIG. 2 shows further protection mechanisms for protection of the EMAT against mechanical damage. A bracket 192, which in each case projects forward and backward in the longitudinal direction, is attached with the aid of screws 191 to the upper face, facing away from the probe unit, of the housing 117 of the magnetization unit, to each of the free ends of which bracket 192 skids 193 are screwed, which project downward, that is to say in the direction of the test object. Seen in the longitudinal direction, these skids are each respectively located before and behind the skids 175 fitted to the probe unit, and overhang these on the outside. Supporting sections 195 which are rounded on the outside are formed in the end sections facing the test object. The brackets 192, with the skids 193 fitted to them, act as spacers 190 for directly supporting the magnetization unit on the surface of the test object, and are of such a size, with respect to the supporting height, that, when the supporting sections 195 make touching contact with the surface 161 of the test object, the probe unit can be forced only so far in the direction of the magnetization unit that a finite minimum separation remains between the magnetization unit and the probe unit, and they cannot touch one another. If a touching contact occurs, then the contact takes place between the magnetization unit and the inside of the elastic bellows material, which forms an elastically flexible intermediate layer in this area, and can damp any impacts. It is therefore possible to use the EMAT to even test very uneven surfaces of the test object, on test objects which may not be perfectly linear, without the risk of damage to the EMAT.

As already mentioned, during the scanning of the surface of the test material, the air gap 125 between the probe unit 120 and the magnetization unit 110 may vary as a function of the condition of the surface of the test material and the linearity of the item being tested. If the discrepancy from linearity is major, it could now be possible for the air gap 125 to disappear completely, thus forcing the probe unit against the magnetization unit. If the holder for the magnetization unit is designed to be flexible to a certain extent, although further movement away is still possible in this case, as before, the probe unit 120 and the magnetization unit 110 would then, however, be moved jointly, and the large magnetic attraction force between the magnetization unit and the test material would now also act on the probe unit, which would significantly reduce the life of the probe unit. This is prevented by the spacers 190. This is because the skids 193 are attached to the ends of the brackets 192 and are of such a size that they make touching contact with the surface of the test material before the air gap 125 disappears completely. This prevents a greatly increased force from acting on the probe unit in the case of very highly curved test material, thus ensuring long lives.

Figure 3:
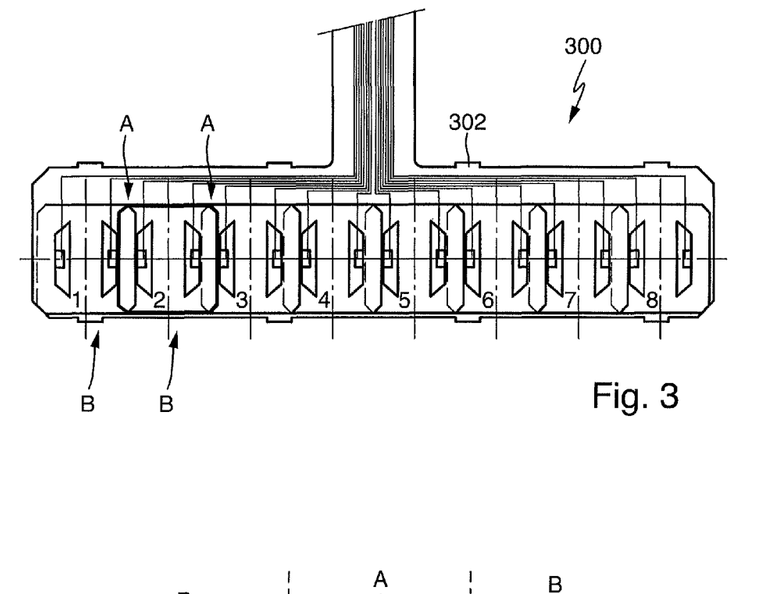
FIG. 3 illustrates a plan view of one example of a coil arrangement.
Figure 4:
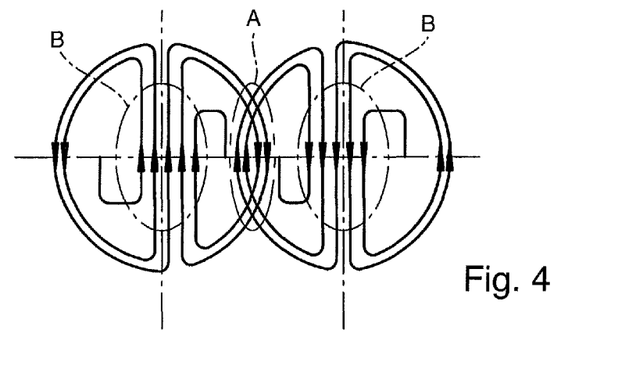
FIG. 4 shows a schematic illustration of an antiphase excitation of immediately adjacent individual coils in the coil arrangement.

FIG. 3 shows one of numerous options for the design of an inductive coil arrangement. The coil arrangement 300 is fitted in the form of printed conductor tracks to a flexible mount 302 composed of electrically insulated plastic. The illustration shows an arrangement with eight coils, which are arranged on a straight line. The shape of the second coil from the left (No. 2) is emphasized by bold lines, for illustrative purposes. Each of the coils has a symmetrical structure with an area B in the center, in which the conductor tracks run parallel and in the same direction. The return lines are split into a part on the right and a part on the left of the central area B. The current flows through the conductor tracks in the opposite direction there. The return line areas of immediately adjacent coils overlap one another in overlap areas A. For illustrative purposes, FIG. 4 schematically illustrates two immediately adjacent inductive coils, in a simplified form. The illustration in this case shows the current directions in two adjacent coils in the central areas B which are directly adjacent, and in the return lines which are located centrally between them and physically overlap in an overlap area A. The current direction arrows indicate that the immediately adjacent probes are excited with AC voltage in antiphase, that is to say with a 180° phase shift, such that the return lines which are located in the overlap area A of the two adjacent inductive coils have current flowing through them in opposite directions. If a plurality of coils are now arranged overlapping such that the return lines of adjacent coils are located precisely one above the other, then the contributions of the return lines cancel one another out when the inductive coils are excited at the same time, but with an alternating phase from one coil to the next.

There is no need to provide magnetic field concentrators between the magnet system of the magnetization unit and the coil arrangement of the probe unit, particularly under these conditions. In conventional electromagnetic acoustic transducers, so-called magnetic field concentrators are provided between the magnet system and the coil arrangement to in each case concentrate the magnetic flux produced by the magnet system into the central areas of the coils of a coil arrangement (corresponding to the areas B in FIG. 4), and to subject the return lines to the magnetic field as little as possible. In contrast, no magnetic field concentrators are required when the inductive coils are arranged such that the return lines overlap, since the contributions of the return lines cancel one another out. Other configurations of coil arrangements are also possible, in which there is no need for magnetic field concentrators. The sound field produced in the material of the test object will then in general run differently than in systems with concentrators.

A coil arrangement similar to the arrangement shown in FIG. 3 can be achieved both by providing a plurality of wound individual coils and by the illustrated implementation of a corresponding conductor structure on an insulating mount in a single component.

Operation without magnetic field concentrators is also possible with this arrangement of the inductive coils or with in-phase excitation. For example, if the coil arrangement illustrated in FIG. 3 is operated in such a way that all the coils are operated in phase, then the current flows through the two return line areas, which are located one above the other, between immediately adjacent coils in the opposite direction to that in the center parts B of the adjacent coils. The result of this is as if there were a further layer between two coils of a coil arrangement, which is operated in antiphase to the two respectively adjacent coils.

Figure 5:
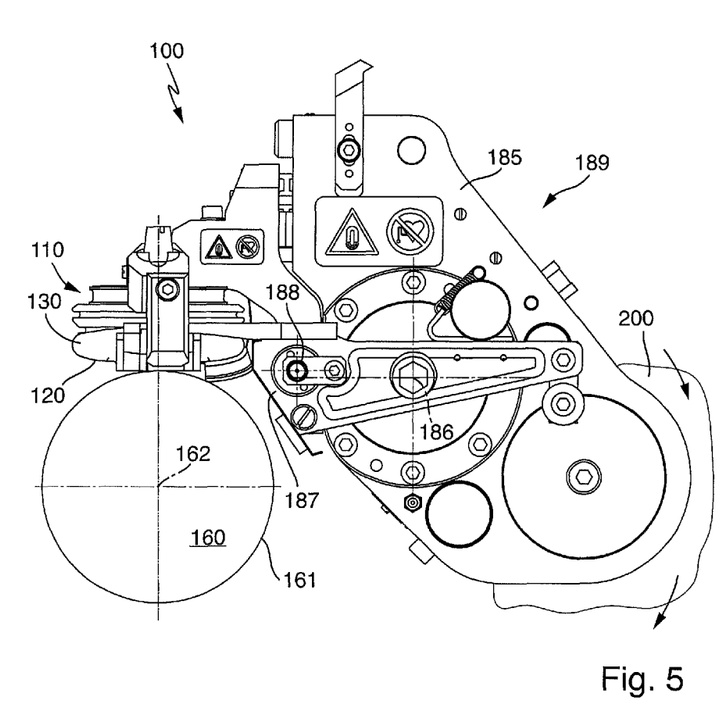
FIG. 5 shows an electromagnetic acoustic transducer with holding devices fitted to it, for installation in a rotating head of a test apparatus.

Electromagnetic acoustic transducers of the type described here with reference to a number of examples can be used for widely differing test tasks and can be implemented in test apparatuses with widely differing designs. FIG. 5 illustrates an implementation as can be used, for example, to test for core flaws in rod material. The test object 160 is moved along its longitudinal axis 162 at high speed (for example, several m/s) through the test apparatus. The test apparatus has a rotating head on which a plurality of electromagnetic acoustic transducers are arranged with the aid of lever arrangements which can pivot, such that the transducers make a sliding contact with the surface 161 of the test object (in other examples, there is a small air gap between the two) and these scan along helical paths during rotation of the rotating head, which parts can abut against one another or overlap if the rotation speed of the rotating head is appropriately matched to the speed at which the test object passes through to ensure that the test object is tested without any gaps. The basic design of rotating heads is known per se, and would therefore not be described in any more detail here. FIG. 5 shows only a part of the rotor 200 of the rotating head, which rotates coaxially with the longitudinal axis 162 of the test object.

The electromagnetic acoustic transducer 100 is attached to the rotor 200 with the aid of a pivoting lever arrangement 189, such that it can pivot. The EMAT comprises the probe unit 120, which makes a sliding contact with the surface of the test object during operation, the magnetization unit 110 which is arranged at a radial distance therefrom, and the flexible bellows 130 as a flexible connection between these assemblies, which are separated from one another and can move relative to one another. The magnetization unit 110 is attached to a first holding device 185 in the form of a pivoting lever, which is mounted on the rotor 200 such that it can rotate about a rotation axis 186, and can move slightly about this axis. The probe unit 120 is attached to a second holding device 187 in the form of a pivoting lever, which is attached to the pivoting lever 185, that is to say to the first holding device, such that it can pivot, and can rotate slightly with respect thereto about a rotation axis 188. When the first holding device 185 pivots, the entire EMAT is moved in the direction of the test object, and away from it. Every relative movement of the probe unit toward the magnetization unit or away from the magnetization unit is in contrast associated with pivoting of the second holding device 187 with respect to the first holding device 185, with the holding device guiding the movement of the probe unit such that it is not tilted or rotated in the axial direction, but essentially carries out only a translational movement toward or away from the magnetization unit. In this case, the second holding device represents a passive guide. The relative movement of the probe unit with respect to the magnetization unit is controlled exclusively by the surface condition of the test object, which, if appropriate, leads to deflection of the probe unit sliding on it with respect to the magnetization unit.

For mechanical and test reasons, it is generally worthwhile fitting to the rotor an arrangement, which is identical to the illustrated arrangement, but offset through 180° with respect to the illustrated arrangement on the rotor, thus creating a balanced test arrangement overall, which can rotate around the test object as it passes through, at a high rotation speed.

The invention claimed is:

1. An electromagnetic acoustic transducer for ultrasound testing of test objects which are composed substantially of an electrically conductive material comprising:
    a magnet system that produces a magnetic field intended to penetrate into the test object, and
    an inductive coil arrangement that produces an electromagnetic alternating field superimposed on this magnetic field in the test object, and that detects electromagnetic alternating fields emitted from the test object,
    wherein the magnet system is arranged in a magnetization unit, the coil arrangement is arranged in a probe unit separate from the magnetization unit, and the probe unit is mounted such that it can move relative to the magnetization unit in the area of the magnetic field.

2. The transducer as claimed in claim 1, wherein an intermediate space of variable size is located between the magnetization unit and the probe unit, and the intermediate space is encapsulated in a contamination-proof manner with a flexible casing.

3. The transducer as claimed in claim 2, wherein the flexible casing has a plastic or leather bellows composed of flexible material.

4. The transducer as claimed in claim 1, wherein the probe unit is attached to the magnetization unit with an elastically flexible holder, wherein the elastically flexible holder has a bellows which seals an intermediate space between the magnetization unit and the probe unit in a contamination-proof manner.

5. The transducer as claimed in claim 1, wherein the magnetization unit is attached to a first holding device and the probe unit is attached to a second holding device separate from the first holding device, and the second holding device, which holds the probe unit, is connected in an articulated manner to the first holding device.

6. The transducer as claimed in claim 1, wherein an intermediate space between the magnet system and the coil arrangement is free of magnetic field concentrators.

7. The transducer as claimed in claim 1, wherein a nominal distance between the magnet system and the coil arrangement is less than 8 mm.

8. The transducer as claimed in claim 1, wherein at least one spacer device limits mutual deflection of the magnetization unit and the probe unit to a finite minimum separation.

9. The transducer as claimed in claim 1, wherein an impact-damping device composed of elastically flexible material is arranged between the magnetization unit and the probe unit.

10. The transducer as claimed in claim 1, wherein spacers with supporting sections that directly support the magnetization unit on a surface of the test object are fitted to a housing of the magnetization unit, and the spacers are sized such that, when the spacers strike the surface of the test object, a finite separation remains between the magnetization unit and the probe unit which has been deflected to the maximum extent in the direction of the magnetization unit.

11. The transducer as claimed in claim 1, wherein the coil arrangement has a plurality of individual coils arranged alongside one another, and line sections of immediately adjacent individual coils overlap one another into an overlap area.

12. The transducer as claimed in claim 1, wherein the coil arrangement has a plurality of individual coils which are arranged alongside one another, and immediately adjacent individual coils of the coil arrangement are switched in antiphase.

13. The transducer as claimed in claim 1, wherein the coil arrangement has conductor tracks fitted to a mount composed of electrically insulating material.

14. A test apparatus for ultrasound testing of test objects composed substantially of electrically conductive material comprising at least one electromagnetic acoustic transducer as claimed in claim 1.

15. An electromagnetic acoustic transducer for ultrasound testing of test objects which are composed substantially of an electrically conductive material comprising:
    a magnet system that produces a magnetic field intended to penetrate into the test object, and
    an inductive coil arrangement that produces an electromagnetic alternating field superimposed on this magnetic field in the test object, and that detects electromagnetic alternating fields emitted from the test object,
    wherein the magnet system is arranged in a magnetization unit, the coil arrangement is arranged in a probe unit separate from the magnetization unit such that the probe unit is always located in the area of the magnetic field produced by the magnet system and the probe unit is mounted such that it can move relative to the magnetization unit in the area of the magnetic field when the transducer is operated.

* * * * *